US010806755B2

(12) United States Patent
Meidler et al.

(10) Patent No.: US 10,806,755 B2
(45) Date of Patent: Oct. 20, 2020

(54) PLASMA-SUPPLEMENTED FORMULATION

(71) Applicant: Omrix Biopharmaceuticals Ltd., Rehovot (IL)

(72) Inventors: Roberto Meidler, Rehovot (IL); Elena Grimberg, Rehovot (IL); Oleg Belyaev, Barnaul (RU); Yonit Tiberman, Nes Ziona (IL); Israel Nur, Moshav Timmorim (IL); Tamar Auerbach-Nevo, Rehovot (IL)

(73) Assignee: Omrix Biopharmaceuticals, Ltd., Rehovot (IL)

( * ) Notice: Subject to any disclaimer, the term of this patent is extended or adjusted under 35 U.S.C. 154(b) by 0 days.

(21) Appl. No.: 14/631,099

(22) Filed: Feb. 25, 2015

(65) Prior Publication Data
US 2015/0238529 A1 Aug. 27, 2015

Related U.S. Application Data

(60) Provisional application No. 61/945,167, filed on Feb. 27, 2014.

(30) Foreign Application Priority Data

Feb. 27, 2014 (IL) .......................................... 231230

(51) Int. Cl.
| | | |
|---|---|---|
| A61K 35/16 | (2015.01) | |
| A61K 38/48 | (2006.01) | |
| A61K 38/36 | (2006.01) | |
| C07K 14/75 | (2006.01) | |
| A61L 24/10 | (2006.01) | |
| A61L 24/00 | (2006.01) | |

(52) U.S. Cl.
CPC ............ *A61K 35/16* (2013.01); *A61K 38/363* (2013.01); *A61K 38/4833* (2013.01); *A61L 24/0005* (2013.01); *A61L 24/10* (2013.01); *A61L 24/106* (2013.01); *C07K 14/75* (2013.01); *C12Y 304/21005* (2013.01)

(58) Field of Classification Search
None
See application file for complete search history.

(56) References Cited

U.S. PATENT DOCUMENTS

| | | | |
|---|---|---|---|
| 4,297,344 A | | 10/1981 | Schwinn et al. |
| 4,341,764 A | | 7/1982 | Wallace et al. |
| 4,455,300 A | | 6/1984 | Wallace et al. |
| 4,627,879 A | * | 12/1986 | Rose .................. A61L 24/0015 106/124.1 |
| 5,318,524 A | | 6/1994 | Morse et al. |
| 5,716,645 A | | 2/1998 | Tse et al. |
| 5,750,657 A | | 5/1998 | Edwardson et al. |
| 5,792,835 A | | 8/1998 | Tse et al. |
| 5,834,420 A | | 11/1998 | Laub |
| 6,262,236 B1 | | 7/2001 | Edwardson et al. |
| 6,268,483 B1 | | 7/2001 | Edwardson et al. |
| 6,277,961 B1 | | 8/2001 | Hock et al. |
| 6,500,427 B1 | | 12/2002 | Heimburger et al. |
| 7,125,569 B2 | | 10/2006 | Nur et al. |
| 8,367,802 B2 | | 2/2013 | Falus et al. |
| 2005/0118156 A1 | | 6/2005 | Woolverton |
| 2005/0252867 A1 | * | 11/2005 | Baugh .................. A61L 24/0005 210/782 |
| 2006/0261014 A1 | * | 11/2006 | Blasetti ............... A61L 26/0042 210/787 |
| 2007/0014780 A1 | | 1/2007 | Woolverton |
| 2008/0044852 A1 | * | 2/2008 | Kanayinkal .......... C07K 14/745 435/68.1 |
| 2011/0033554 A1 | * | 2/2011 | Burnouf ................. A61K 35/16 424/529 |
| 2015/0238529 A1 | | 8/2015 | Roberto et al. |
| 2017/0037108 A1 | | 2/2017 | Bout et al. |

FOREIGN PATENT DOCUMENTS

| | | |
|---|---|---|
| AU | 2015221786 A1 | 8/2019 |
| CN | 1617735 A | 5/2005 |
| CN | 102089322 A | 6/2011 |
| EP | 1393741 | 3/2004 |
| JP | 6563412 B2 | 8/2019 |
| WO | WO 1993/05822 | 4/1993 |
| WO | WO 1994/22503 | 10/1994 |
| WO | WO 98/55140 * | 6/1998 |
| WO | WO 2003/028654 | 4/2003 |
| WO | WO 2009/155626 | 12/2009 |
| WO | WO 2010/004004 | 1/2010 |
| WO | WO 2013/001524 | 1/2013 |
| WO | WO 2013039411 * | 3/2013 |

OTHER PUBLICATIONS

Saifer et al., "Photometric Microdetermination of Plasma Fibrinogen with a Thrombin-Ninhydrin Procedure", http: // www.jbc.org/ , Journal of Biol. Chem., 1954, vol. 208, pp. 159-179.*
Clauss A. 'Gerinnungsphysiologische Schnellmethode zur Bestimmung des Fibrinogens.' Acta Haematol. (1957) 17 pp. 237-246.
Dickneite, G. et al. 'A comparison of fibrin sealants in relation to their in vitro and in vivo properties.' Thrombosis Res (2003) 112 pp. 73-82.
Fibrin sealant kit. European Pharmacopoeia. (1997) 0903 pp. 857-858.
Guerrier L. et al. 'Specific sorbent to remove solvent-detergent mixtures from virus-inactivated biological fluids' J Chromatogr B: Biomed Appl. (1995) 664(1) pp. 119-125.
Lacci KM, Dardik A. 'Platelet-Rich Plasma: Support for Its Use in Wound Healing.' Yale J Biol Med. (2010) 83(1) pp. 1-9.
Raccuia J.S. et al., 'Comparative Efficacy of Topical Hemostatic Agents in a Rat Kidney Model.' Am J Surg. (1992) 163(2) pp. 234-238.
Tabélé, C. et al., 'Organic Glues or Fibrin Glues from Pooled Plasma: Efficacy, Safety and Potential as Scaffold Delivery Systems' J Pharm Pharmaceut Sci (2012) 15 pp. 124-140.
International Search Report re: PCT/IL2015/000010 dated Jun. 2, 2015.

(Continued)

*Primary Examiner* — Laura Schuberg
(74) *Attorney, Agent, or Firm* — David R. Crichton

(57) ABSTRACT

Provided herein is a plasma-supplemented fibrinogen and/or fibrin formulation, method for the preparation and use thereof.

5 Claims, 1 Drawing Sheet

(56) References Cited

OTHER PUBLICATIONS

Company Core Data Sheet—CCDS (EDS/Core/English) Haemocompettan P1g/2g, May 22, 2014, XP055400649, Retrieved from the Internet: URL:http://labeling.cslbehring.com/CCDS/CORE/Haemocomplettan-P/EN/Haemocompettan-P-Data-Sheet.pdf.
International Preliminary Report on Patentability for application No. PCT/IL2015/000010 dated Aug. 30, 2016, pp. 7.
Chinese First Office Action for application No. CN21580010752 dated, Nov. 1, 2018, pp. 13(English Translation Provided).
ChineseSecond Office Action for application No. CN21580010752 dated, Apr. 18, 2019, pp. 13(English Translation Provided).
European Examination Report for application No. EP15717659 dated Aug. 29, 2017, pp. 5.

\* cited by examiner

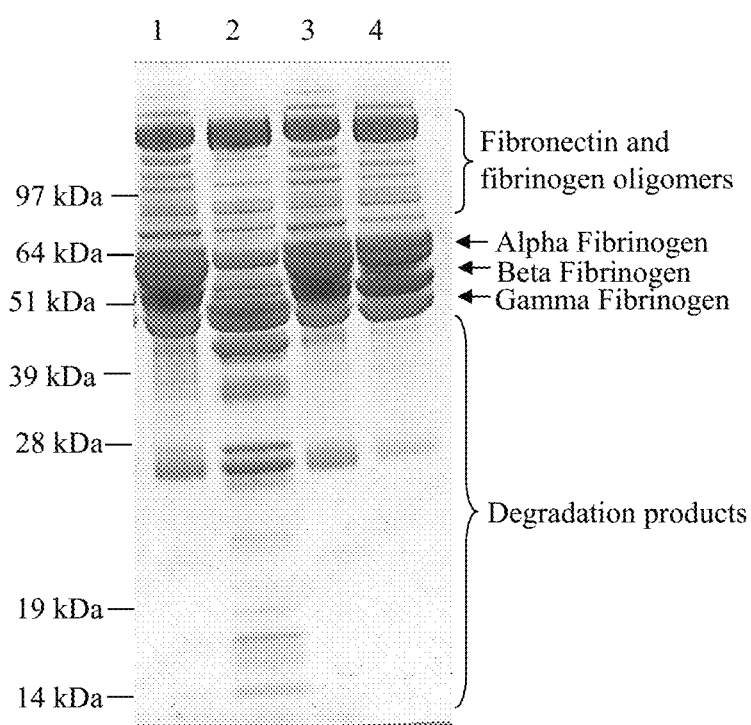

PLASMA-SUPPLEMENTED FORMULATION

FIELD OF THE INVENTION

Provided herein is a method for the preparation of a plasma-supplemented fibrinogen and/or fibrin formulation, a plasma-supplemented fibrinogen and/or fibrin formulation and methods of use therewith.

BACKGROUND

Fibrin sealants, also known as fibrin glue, have been in use in the clinic for decades (see, for example, Tabélé, et. al., J Pharm Pharmaceut Sci 2012, 15:124-140; Dickneite, G et al. Thrombosis Res 2003, 112:73-82). Oftentimes, fibrin sealant consist of two liquid components, a fibrinogen comprising component and a thrombin comprising component, which are stored frozen due to their inherent instability. Sometimes fibrin sealant products consist of two freeze dried components, which require reconstitution immediately prior to use and delivery by a conjoined syringe or other double-barreled delivery device. Freeze dried formulations are typically stable, but the fibrinogen component is difficult to reconstitute.

A fibrin sealant clot is formed by enzymatic reactions involving fibrinogen, thrombin and Factor XIII. The thrombin converts the fibrinogen to fibrin by enzymatic action at a rate determined by the thrombin concentration. Factor XIII, an enzyme of the blood coagulation system, cross-links and stabilizes the fibrin clot. This process bypasses most of the steps of normal coagulation and mimics its last phase. Some manufacturers add anti-proteolytic agents to the fibrin formulation (e.g. as described in WO 93/05822) or specifically remove the plasminogen in order to stop or delay fibrinolysis (e.g. as described in U.S. Pat. Nos. 5,792,835 and 7,125,569). The fibrinogen and thrombin components can be from human or animal (e.g. bovine or porcine) origin or may be recombinantly produced. Upon mixing the two-component solutions, thrombin cleaves fibrinogen thus allowing the latter to polymerize into fibrin and generate the sealant. The thrombin component contains the enzyme thrombin, which is a serine protease.

The production process of certain industrial fibrinogen fractions results in the partial or complete removal of some of the plasma proteins from the fibrinogen composition. A case in point is the production of a fibrinogen containing fraction obtained as a by-product during the manufacturing process of Factor VIII (FVIII). Although this fibrinogen-enriched fraction may be utilized to obtain a fibrinogen composition useful as a component of a fibrin sealant, the fraction may be partially or totally depleted from some of the plasma proteins during the process steps. As a result, the fibrinogen composition obtained from such a fibrinogen-enriched fraction has low levels, or completely lacks important plasma proteins.

Background art includes U.S. Pat. Nos. 4,341,764; 4,455,300; 5,834,420 and 6,277,961.

SUMMARY OF THE INVENTION

Provided herein is a method for the preparation of plasma-supplemented fibrinogen, a plasma-supplemented fibrinogen and use thereof for the manufacture of a component of a sealant formulation.

Also, provided herein are methods for the manufacture of a fibrinogen formulation, the fibrinogen formulation per se and use therewith, inter alia, as a fibrinogen component in a tissue sealant formulation.

In one aspect, provided herein is a method of preparing a fibrinogen formulation, the method comprising the step of mixing a concentrated fibrinogen preparation and a blood plasma source. A concentrated fibrinogen preparation relates to a preparation which comprises a fibrinogen concentration which is higher than the fibrinogen concentration in blood or plasma (greater than about 2-4 mg/ml and e.g. up to 200 mg/ml). The concentrated fibrinogen preparation can be obtained from, for example, a mammalian origin (e.g. human or pig) or can be recombinant. In some embodiments, the concentrated fibrinogen preparation is derived from blood or a blood fraction. In some embodiments, the concentrated fibrinogen preparation is derived from human blood or a human blood fraction.

In various embodiments of the method, the concentration of fibrinogen in the concentrated fibrinogen preparation is about 10 mg/ml to about 200 mg/ml, for example, about 10 mg/ml to 150 mg/ml; about 20-40 mg/ml; about 15-40 mg/ml; about 20-150 mg/ml; about 30 mg/ml; or about 25-120 mg/ml. In some embodiments, the concentrated fibrinogen preparation is a cryoprecipitate. In various embodiments, the cryoprecipitate is a Factor VIII-depleted cryoprecipitate (FDC). After mixing with a solution comprising a plasma source, the fibrinogen concentration can be in the range of 7 mg/ml to 150 mg/ml, about 20-40 mg/ml; about 15-40 mg/ml; about 25-120 mg/ml, or about 30 mg/ml.

In some embodiments of the method, the plasma source is, for example, animal plasma, for example mammalian plasma, preferably human plasma. In some embodiments, the plasma source is pooled animal plasma; for example, pooled human plasma. In one embodiment, the plasma source is cryo-poor plasma. Cryo-poor plasma is pooled plasma from which cryoprecipitate was removed. Typically, plasma contains growth factors. In one embodiment the plasma source and/or the fibrinogen is/are non-autologous. In certain embodiment, the plasma is not platelet rich plasma.

The term "platelet rich plasma" (PRP) typically relates to an ex vivo preparation consisting of platelets concentrated in a limited volume of plasma (Lacci K M, Dardik A. Platelet-rich plasma: support for its use in wound healing. Yale J Biol Med. 2010. March; 83(1):1-9).

The term "autologous" means derived from the same individual or involving one individual as both donor and recipient.

In one embodiment the plasma is thrombin free and/or Factor depleted plasma.

"Factor depleted plasma" relates herein to plasma depleted in one or more coagulation factors such as Factor II, Factor X, Factor V.

"Factor-II depleted plasma" or "Factor II Deficient Plasma" or "Prothrombin Deficient Plasma" is manufactured from pooled normal human plasma depleted of Factor II or Prothrombin. The activity of prothrombin remaining may be e.g. less than or equal to, 10% or less than or equal to 1%.

The term "thrombin free plasma" relates to a plasma having activity of thrombin e.g. of equal to or less than 2 IU/ml or undetectable according to a clotting time assay or chromogenic assay.

In various embodiments, the concentrated fibrinogen preparation and the plasma source are mixed in a ratio of about 3:1 to about 1:3 (w/v, v/v, or w/w), about 2:1 to about 1:2 (w/v, v/v, or w/w), or about 1:1 (w/v, v/v, or w/w).

In another aspect, provided is a fibrinogen formulation comprising a fibrinogen preparation supplemented with plasma. In some embodiments, the fibrinogen formulation is prepared by mixing a concentrated fibrinogen preparation and a blood plasma source. A concentrated fibrinogen preparation relates to a preparation which comprises a fibrinogen concentration which is higher than the fibrinogen concentration in blood or plasma for example, greater than about 2-4 mg/ml and e.g. up to about 200 mg/ml. The concentrated fibrinogen preparation can be obtained from, for example, a mammalian origin (e.g. human or pig) or can be recombinant. In some embodiments, the concentrated fibrinogen preparation is derived from blood or a blood fraction. In some embodiments, the concentrated fibrinogen preparation is derived from human blood or a human blood fraction.

In various embodiments, the concentration of fibrinogen in the concentrated fibrinogen preparation is about 10 mg/ml to about 200 mg/ml, for example, about 10 mg/ml to 150 mg/ml; about 20-40 mg/ml; about 20-150 mg/ml; about 30 mg/ml; or about 25-120 mg/ml. In some embodiments, the concentrated fibrinogen preparation is a cryoprecipitate. In various embodiments, the cryoprecipitate is a Factor VIII-depleted cryoprecipitate (FDC). After mixing with a solution comprising a plasma source, the fibrinogen concentration can be in the range of 7 mg/ml to 150 mg/ml, about 20-40 mg/ml; about 15-40 mg/ml; about 25-120 mg/ml, or about 30 mg/ml.

In some embodiments, the plasma source is animal plasma, preferably mammalian plasma for example human plasma. In some embodiments, the plasma source is pooled animal plasma, for example pooled human plasma (e.g. cryo-poor plasma). In various embodiments, the concentrated fibrinogen preparation and the plasma source are mixed in a ratio of about 3:1 to about 1:3 (w/v, v/v, or w/w), or about 2:1 to about 1:2 (w/v, v/v, or w/w), or about 1:1 (w/v, v/v, or w/w).

In some embodiments, the fibrinogen formulation is in liquid form. In some embodiments, the fibrinogen formulation comprises a pharmaceutically acceptable carrier. In one embodiment, the fibrinogen concentration in the formulation is in the range of 50 to 120 mg/ml. In another embodiment, the fibrinogen concentration in the formulation is in the range of 50 to 90 mg/ml or 55 to 85 mg/ml, about 70 mg/ml, in the range of 7 mg/ml to 150 mg/ml, about 20-40 mg/ml; about 15-40 mg/ml; about 25-120 mg/ml, or about 30 mg/ml.

The fibrinogen formulation is preferably sterile and free from pathogens, for example by S/D treatment, pasteurization and/or filtration. In various embodiments, the fibrinogen formulation is lyophilized.

In another aspect, provided is a container holding a plasma-supplemented fibrinogen formulation. The container may be for example, an ampoule, a vial or syringe. The containers can be made of for example, glass, metal or plastic.

In another aspect, provided is a kit comprising a container such as an ampoule, a vial or syringe which includes the plasma-supplemented fibrinogen formulation as disclosed hereinabove; optionally the kit includes a thrombin component and/or instructions for use. In some embodiments, provided is a kit that comprises a container with a concentrated fibrinogen preparation; and a container with plasma. The kit may further include a thrombin component and/or instructions for use. The kit may include at least one container and at least one label. Examples of suitable containers include, but are not limited to, ampoules, vials, syringes and test tubes.

The plasma-supplemented fibrinogen formulations disclosed hereinabove are useful in formation of a sealant for, for example, hemostasis, healing, and/or surgery, including, without limitation, graft fixation, wound healing, restoration, reconstruction and sealing of anastomosis sites. The fibrinogen formulations can also be used in a sealant for plastic surgery, for example, abdominoplasty; skin and internal organ graft fixation; tissue healing; burn treatment; and/or attenuating wound bleeding. Such a sealant is further useful for dura sealing, for example in cranial or spinal surgery.

Accordingly, in one aspect, provided is a method of providing hemostatic treatment; graft fixation, wound healing and/or anastomosis, to a surface in a subject in need, comprising applying to the surface a therapeutically effective amount of a plasma-supplemented fibrinogen formulation. The method includes, without limitations, abdominoplasty; tissue healing; burn treatment; and dura sealing. The subject may be an animal, for example a mammalian subject, including a human subject.

In another aspect, provided is a plasma-supplemented fibrinogen formulation for use in healing, hemostasis and/or surgery. The uses include, without limitation, graft fixation; wound healing; anastomosis; abdominoplasty; tissue healing; burn treatment; and dura sealing.

In another aspect, provided herein is a method for forming a sealant at a surface comprising applying to the surface a plasma-supplemented fibrinogen component and a thrombin component.

In another aspect, provided herein is a method for forming a sealant. The method comprises using plasma-supplemented fibrinogen.

In yet another aspect, provided herein is a method for manufacturing a component for a sealant formulation, the method, comprising a step of mixing a concentrated fibrinogen preparation with a plasma source.

The sealant formulation can be a one component sealant formulation, or a multi-component sealant formulation such as a two-component sealant formulation or more. Examples of a one component sealant formulation include U.S. Pat. Nos. 5,318,524, 8,367,802, 6,262,236 B1, 6,268,483 B1, 5,750,657A, 6,500,427 B1. In one embodiment the one component sealant is a stable liquid sealant formulation comprising fibrin monomers and a reversible fibrin polymerization blocking agent. In one embodiment, a single component sealant formulation includes fibrinogen; and vitamin K-dependent clotting zymogens such as Factor II (FII) and Factor X (FX).

The surface can be a bleeding or non-bleeding surface in a subject. The surface may also be for example, a bodily surface, an external or internal body organ, a blood vessel or a graft tissue or organ. The subject may be an animal, for example a mammalian subject, including a human subject.

In certain embodiments, the plasma source in the various aspects of the invention is not a cryoprecipitate.

These and other aspects and embodiments of the invention will become evident upon reference to the following detailed description of the invention and the figures.

BRIEF DESCRIPTION OF THE FIGURE

FIG. 1 shows a comparison of fibrinogen formulations which are un-supplemented (lanes 2 and 4) or have been supplemented (lanes 1 and 3) with plasma kept for 5 days at 37° C. (lanes 1 and 2) or at −80° C. (lanes 3 and 4) as assayed by SDS-PAGE.

DETAILED DESCRIPTION OF THE INVENTION

The present invention is based in part upon the unexpected finding that supplementation of a concentrated fibrinogen preparation with blood plasma results in a stable fibrinogen formulation useful, inter alia, as a component of a biological sealant. Hitherto, fibrinogen or fibrinogen containing fractions have been isolated from plasma to generate fibrinogen formulations for use in tissue sealants, hence the manufacture of a fibrinogen formulation comprising the addition of a blood plasma source to a concentrated fibrinogen preparation is counterintuitive and would be considered contamination of the formulation e.g. by proteases. Furthermore, the blood plasma-supplemented fibrinogen formulation exhibits surprising stability compared to un-supplemented fibrinogen formulations.

Stability of the fibrinogen formulation can be determined for example by observing the gel separation pattern of the formulation, by comparing fibrinogen concentration by Clauss over time or by the ability of the formulation to form a clot.

Disclosed herein are: a method of manufacturing a fibrinogen formulation comprising the step of mixing a concentrated fibrinogen preparation and a plasma source, the plasma-supplemented fibrinogen formulation per se, and methods of using the plasma-supplemented fibrinogen formulation.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%. The term "g" refers to gram, "mg" refers to milligram and "ml" refers to milliliter.

The term sealant as used herein is interchangeable with the term glue.

A "concentrated fibrinogen preparation" relates to a preparation which comprises a fibrinogen concentration which is higher than the fibrinogen concentration in blood or plasma such as greater than about 2-4 mg fibrinogen per ml and up to about 200 mg fibrinogen per ml. A concentrated fibrinogen preparation includes, for example, about 20-40 mg/ml; about 15-40 mg/ml; about 10-200 mg/ml; 10-150 mg/ml; 20-150 mg/ml; about 30 mg/ml; or about 25-120 mg/ml. A concentrated fibrinogen preparation may be prepared from any origin, for example, mammalian origin (e.g. from human blood plasma or pig plasma) or may be recombinant. In some embodiments, the concentrated fibrinogen preparation is a cryoprecipitate. After mixing with a solution comprising a plasma source, the fibrinogen concentration can be in the range of 7 mg/ml to 150 mg/ml, about 20-40 mg/ml; about 15-40 mg/ml; about 25-120 mg/ml, or about 30 mg/ml.

In one embodiment of the invention a "concentrated fibrinogen preparation" is a purified fibrinogen preparation. Purified fibrinogen preparation is obtained from a starting composition comprising fibrinogen and subjecting the starting composition to one or more purification step (such as a chromatographic step, or precipitation step) resulting into a preparation enriched with fibrinogen when compared to the starting composition.

The term "cryo-poor plasma" refers to pooled plasma from which cryoprecipitate was removed.

Concentration of functional fibrinogen can be measured by the modified European Pharmacopeia Assay (0903/1997) procedure as elaborated in: European Pharmacopoeia, Fibrin sealant kit. 1997; 0903:858; and Clauss A. Gerinnungsphysiologische Schnellmethode zur Bestimmung des Fibrinogens. Acta Haematol. 1957; 17: 237-246; by ability to form a clot or by any other methods known in the art.

The term "cryoprecipitate" refers to a blood component which is obtained from frozen plasma prepared from whole blood, recovered plasma or from plasma which is collected by plasmapheresis. A cryoprecipitate can be obtained when frozen plasma is slowly thawed in the cold, typically at a temperature of 0-4° C., resulting in the formation of a precipitate that contains fibrinogen and Factor XIII. The precipitate can be collected, for example by centrifugation.

The precipitate can be a by-product from the manufacture process of FVIII and is termed herein as "FDC" e.g. acid-precipitate, chill-precipitate, aluminum hydroxide precipitate (see, for example, U.S. Pat. No. 4,455,300), glycine precipitate (see, for example, U.S. Pat. No. 4,297,344), ethanol precipitate and heparin precipitated paste.

The term "by-product" refers to an undesired and/or unintended and/or non-used material and/or residual material usually produced or formed in the course of an industrial or biological process in addition to the desired material/product.

The term "precipitate" and "precipitated fraction" are interchangeable.

In one embodiment, the precipitate is an aluminum hydroxide precipitate. Advantageously, when a precipitate comprises aluminum hydroxide, the aluminum hydroxide can be easily removed from the suspended precipitate together with certain proteases, for example, by centrifugation and/or filtration.

In one embodiment of the invention, the concentrated fibrinogen preparation is at least partially soluble, fully soluble, or fully non-soluble during supplementation with the plasma source.

"Fully soluble" means 100% dissolved e.g. without any solid particles. "Partially soluble" means less than 100% dissolved e.g. the concentrated fibrinogen preparation can be from about 5% to less than 100% dissolved.

In one embodiment of the invention, the concentrated fibrinogen preparation is about 50% to about 95% dissolved.

"Fully non-soluble" means 100% in solid form.

As described herein, the concentrated fibrinogen preparation and the plasma source are mixed in a ratio of about 3:1 to about 1:3 (w/v, v/v, or w/w), or about 2:1 to about 1:2 (w/v, v/v, or w/w), or about 1:1 (w/v, v/v, or w/w). The term "w/v, v/v, or w/w" means that the concentrated fibrinogen preparation and the plasma source may be independently either liquid or solid.

Provided is a method for manufacturing a sealant formulation. The method comprises a step of mixing a concentrated fibrinogen preparation with a plasma source.

Sealant formulations may include one or more components.

A sealant may comprise one component comprising plasma-supplemented fibrinogen and another component comprising thrombin.

Alternatively, a sealant may comprise a component comprising plasma-supplemented fibrinogen and prothrombin.

Also, a sealant may comprise a component comprising fibrin monomers under conditions which inhibit polymerization, e.g. low pH or by including in the composition an inhibitor of polymerization such as GPRP. The fibrin monomers can be prepared from the plasma-supplemented fibrinogen e.g. by contacting the plasma supplemented fibrinogen with thrombin coupled to beads and collecting an unbound fraction.

Fibrinogen, thrombin and plasma can be contacted under conditions which inhibit fibrin polymerization.

Plasma can be used to stabilize and/or add important plasma proteins to a liquid sealant formulation comprising fibrin monomers.

Provided herein is a plasma-supplemented liquid sealant formulation comprising fibrin monomers. Further provided herein is a plasma-supplemented liquid sealant formulation comprising: a) fibrin monomers; and b) a reversible fibrin polymerization blocking agent.

In one embodiment, a reversible inhibitor relates to a low affinity of the inhibitor (e.g. GPRP peptide) to fibrin monomer and having no permanent effects on fibrin polymerization or fibrin clot. Therefore, typically, dilution and/or removal will remove the inhibitory effect.

Examples of reversible fibrin polymerization inhibitory gent include but are not limited to a GPRP peptide, pH, and an aptamer.

The term "fibrin monomers" as used herein includes fibrin monomers, dimers and/or oligomers having a number of fibrin units so that the fibrin is maintained in soluble form in an aqueous liquid solution at an ambient temperature selected from the group consisting of about 20, 21, 22, 23, 24, and 25° C. In one embodiment, an oligomer contains up to 10 fibrin units.

The term "fibrin polymer" as used herein includes a plurality of fibrin units having a number of fibrin units that limit the solubility of the fibrin in an aqueous liquid solution at an ambient temperature selected from the group consisting of about 20, 21, 22, 23, 24, and 25° C.

Also, provided herein is a plasma-supplemented fibrinogen and/or plasma-supplemented liquid sealant formulation comprising fibrin monomers which can be administered as a stand-alone formulation to a subject in need.

Provided is a fibrin sealant formulation which can be administered to a subject in need.

"Plasma" and "blood plasma" may be used interchangeably and refer to the plasma fraction of blood that contains, inter alia, salts, enzymes, immunoglobulins (antibodies), clotting factors and proteins including albumin, factor VIII and fibrinogen. A "plasma source" may be plasma from fractionation, pooled plasma, cryo-poor plasma, recovered plasma, and plasma which is the fluid portion of human blood collected by plasmapheresis. In one embodiment the plasma is thrombin depleted and/or factor depleted plasma.

Plasma is a fraction of blood. Unfractionated blood is not considered as a "plasma source" as defined in the instant application.

"Thrombin" or "thrombin polypeptide" is a mammalian serine protease which results from the cleavage of prothrombin (Factor II), a zymogen precursor, by another serine protease (Factor Xa). Thrombin is part of the blood coagulation cascade and converts fibrinogen into insoluble strands of fibrin, as well as catalyzes other coagulation-related reactions. In humans, prothrombin is encoded by the F2 gene, and the resulting polypeptide is proteolytically cleaved in the coagulation cascade to form thrombin. Thrombin serves, inter alia, as an active component in several hemostasis products. For example, fibrin sealants typically comprise a fibrinogen component and a thrombin component. When both components are mixed (e.g. when applied to a bleeding wound) thrombin cleaves fibrinogen and a fibrin polymer is formed.

For long-term storage, the fibrinogen formulation is aliquoted into sterile vials, ampoules, or other containers, for example a syringe or other applicator, which are then sealed. In one embodiment, a container that permits removal of the formulation with a syringe through the seal is used. The container is labeled according to standard practice in the pharmaceutical or medical device field.

In another aspect, provided is a kit comprising a container such as an ampoule, a vial or syringe which includes the fibrinogen formulation as disclosed hereinabove; optionally the kit includes a thrombin component and/or instructions for use. A kit may include at least one container and at least one label. Suitable containers include, for example, ampoules, vials, syringes and test tubes. The containers can be made of for example, glass, metal or plastic. In an alternative aspect provided is a kit which includes a container with concentrated fibrinogen preparation and a container with plasma; optionally the kit includes a thrombin component and/or instructions for use.

"Ambient temperature" is the temperature in the surroundings where the fibrinogen formulation is kept.

The fibrinogen formulation may be used as a fibrinogen component for forming biological sealants. For use, the fibrinogen formulation can be used directly from the container according to the needs of the individual patient and on the severity of bleeding. For example, the fibrinogen formulation can be applied to a bleeding tissue concomitantly with a thrombin formulation to achieve hemostasis. Alternatively, the fibrinogen formulation may be used in a single component sealant formulation. In one embodiment, a single component sealant formulation includes fibrinogen; and vitamin K-dependent clotting zymogens such as Factor II (FII) and Factor X (FX).

The formulation according to the present invention can be liquid, frozen or lyophilized.

The advantages of the present formulations are manifold and can be at least one of the following: enhanced stability, enhanced antiviral activity e.g. enriched in anti-B19 specific antibodies, improved healing properties and/or efficient use of concentrated fibrinogen by-product preparations as alternative starting material for fibrin sealants.

A fibrin sealant can be formed from a one-component formulation, a two-component formulation or more.

A "pharmaceutically acceptable carrier or diluent" refers to reagents, compounds, materials, compositions, diluents that are compatible with the constituents in the formulation and suitable for use in contact with the tissues of human beings and animals without excessive toxicity, irritation, allergic response, or other complication commensurate with a reasonable benefit/risk ratio.

A "surface" is a position or location where one desires to form the sealant or glue. The surface depends on the use of the sealant. The sealant may be used, for example, in hemostasis, tissue fixation, graft fixation, wound healing and anastomosis. The formulations, methods, and kits disclosed herein can be used internally and externally, for tissue and organ graft fixation, for sealing a surgical wound, in vascular surgery including providing hemostasis and for anastomoses such as arterial, gastrointestinal and tracheal anastomoses.

The term "animal" as used herein includes mammalian and human subjects.

A "subject" as used herein, includes animals of mammalian origin, including humans. In one embodiment, a subject is a surgery patient or a wounded patient.

A "therapeutically effective amount" means an amount that provides a fibrin sealing effect e.g. sealing, healing and/or reducing blood loss in the subject.

Biological materials derived from blood components are typically purified from infective particles in order to minimize the potential risk posed by blood-borne pathogens. The purification procedure can be carried out by nanofiltration, solvent/detergent (S/D) treatment, heat treatment, gamma or UVC (<280 nm) irradiation, or by any other method known in the art.

The term "infective particle" refers to a microscopic particle, such as, but not limited to, a microorganism or a prion, which can infect or propagate in a biological organism. The infective particles can be viral particles. The inactivation procedure of infective particles can be carried out by adding an inactivating molecule to a solution prior to and/or during the procedure. The added molecules and their products can be removed by gravitation, column chromatography phase separation or by any other method known in the art. The removal of infective particles can be carried out by filtration or by selective absorption methods such as affinity, ion exchange or hydrophobic chromatography.

A multi-step viral inactivation procedure can be carried out. For example, by combining two or more of the following: solvent/detergent treatment, pasteurization, selective chromatography and nanofiltration.

The term "viral inactivation" refers both to the situation wherein viruses are maintained in a solution but are rendered non-viable (for example, by dissolving their lipid coat), and/or to the situation wherein viruses are physically removed from the solution (for example, by size exclusion techniques).

"Solvent detergent (S/D) treatment" typically refers to a process that inactivates enveloped or lipid-coated viruses by destroying their lipid envelope. The treatment can be carried out by the addition of detergents (such as Triton X-45, Triton X-100 or Tween 80) and solvents [such as tri(n-butyl) phosphate (TnBP), di- or trialkylphosphates]. The solvent-detergent combination used to deactivate lipid coated viruses may be any solvent-detergent combination known in the art such as TnBP and Triton X-100; Tween 80 and Sodium cholate and other combinations. The concentration of the solvent(s) and detergent(s) used can be those commonly used in the art, for example, >0.1% TnBP and >0.1% Triton X-100. Sometimes a combination of 1% Triton X-100 and 0.3% TnBP is used. Typically, the conditions under which the solvent-detergent inactivates the viruses consist of 10-100 mg/ml of solvent-detergent at a pH level ranging from 5-8, and a temperature ranging from 2-37° C. for 30 min. to 24 hours. However, other solvent-detergent combinations and suitable conditions will be apparent to a person versed in the art. The bulk of the solvent-detergent used in the S/D treatment can be removed, for example, by using chromatography columns such as hydrophobic interaction chromatography column (HIC) e.g. C-18 silica packing material and SDR (Solvent-Detergent removal) HyperD; protein adsorption matrices such as ion-exchange matrices; affinity matrices; oil extraction and/or size-exclusion matrices. The SDR HyperD advantageously involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

"Pasteurization" typically refers to a process by which heat destroys both lipid-enveloped and non-enveloped viruses. "Pasteurization" is interchangeable with the term "heat inactivation" or "heat treatment". The heat inactivation can be carried out at about 60° C. for about 10 hours. Stabilizers such as sucrose and glycine can be added into a solution during the pasteurization step.

"Nanofiltration" typically refers to a process by which lipid-enveloped and non-enveloped viruses are excluded from a solution e.g. by using nanometer-scale filters such as Planova™ 15N, 20N, 35N and 75N; Viresolve/70™, Viresolve/180™. The filters can have a pore size of less than 70 nm, preferably between 15 and 50 nm. However, any membrane having a pore size sufficient to reduce or eliminate viruses from the sample can be employed in nanofiltration. Viruses removed by nanofiltration can be enveloped (e.g. HIV, hepatitis B virus (HBV), hepatitis C virus (HCV), West Nile Virus, cytomegalovirus (CMV), Epstein-Barr virus (EBV), herpes simplex virus (HSV)), and non-enveloped (e.g. hepatitis A virus, parvovirus B19, Polio virus). The solution can be concentrated by ultrafiltration process. The ultrafiltration can be followed by or preceded by diafiltration to exchange the buffer. The concentration and dialysis by ultrafiltration and diafiltration, respectively, can be carried out in one step or as two separate steps. The diafiltration can be carried out against any solvent or buffer which is suitable for human administration.

The disclosure of applications, patents and publications, cited above or below, is hereby incorporated by reference.

While the following examples demonstrate certain embodiments of the invention, they are not to be interpreted as limiting the scope of the invention, but rather as contributing to a complete description of the invention.

EXAMPLES

Materials and Methods.
Preparation of a Factor VIII Depleted Cryoprecipitate (FDC):

FVIII-depleted cryoprecipitate (FDC) is a by-product of the manufacturing process of Factor VIII (FVIII). During the manufacturing process, fibrinogen, fibronectin, Factor XIII and proteases such as plasmin and/or plasminogen, are precipitated from a resuspended cryoprecipitate by the addition of ethanol under conditions of low salt concentration at a temperature in the range of 14-18° C., followed by centrifugation. Aluminum hydroxide [$Al(OH)_3$] is added during the above re-suspension) prior to the centrifugation step resulting in precipitation of vitamin K dependent coagulation factors such as Factors II, VII and X with the aluminum hydroxide. The aluminum hydroxide precipitate (i.e. FDC) was separated from the Factor VIII-containing supernatant and used in the experiments described below.

The FDC was obtained as follows: A plasma cryoprecipitate was prepared essentially as described in International Patent Application Publication Nos. WO 93/05822 and WO 94/22503.

Briefly, the cryoprecipitate was prepared from frozen (−30° C.) human plasma which was thawed at 4° C. and the supernatant was removed. The cryoprecipitate was kept at −30° C. until use. The cryoprecipitate was thawed at 0-4° C. and re-suspended at 10-20° C. in a double volume of water containing 3 IU/ml sodium heparin (protease inhibitor). The pH was adjusted to 7-8 using diluted acetic acid. Ethanol was added to a final concentration of 1%. The pH was adjusted to 6.8-7.2 using diluted acetic acid. The mixture was cooled to a temperature of 10-15° C. while stirring and aluminum hydroxide was added (108 g of 2% Alhydrogel solution per 1 Kg cryoprecipitate) followed by centrifugation at 17,000 g for 25 min at 14-18° C. The supernatant (containing factor VIII) was removed and the pellet was collected. This precipitate (pellet), also known as the FDC, contained inter alia fibrinogen, Factor XIII, fibronectin, plasmin and/or plasminogen, aluminum hydroxide and vitamin K dependent coagulation factors. The pellet comprised ethanol (~1% ethanol) and had a pH less than 7.2. The pellet was kept at −80° C. until further processing.

This precipitate (FDC) was used as one example of a concentrated fibrinogen preparation.

Determination of Fibrinogen Levels:

Determination of fibrinogen levels by testing clotting time (Clauss method).

The Clauss method is a modification of the European Pharmacopoeia assay 0903/1997, based on the Clauss method, which is a kinematic method assessing the clotting time of the tested sample. A calibration curve was prepared with 1% fibrinogen (Enzyme Research) in the presence of an excess of thrombin and the fibrinogen concentration of the samples are calculated from the calibration curve. The calibration curve was generated for fibrinogen in the range of 8 mg/100 ml to 32 mg/100 ml. The results of the tested samples are reported in mg/ml fibrinogen by multiplying the results by the dilution factor of the samples:

Fibrinogen of Sample (mg/ml)=(mg/100 ml from calibration curve×dilution factor)/100.

Example 1: Plasma Supplementation of Concentrated Fibrinogen Preparation Obtained from FDC Unsupplemented and plasma supplemented fibrinogen samples were prepared as follows: 120 ml and 90 ml of resuspension buffer (0.7% NaCl, 0.295% tri-sodium citrate pH 7.4) were pre warmed to 34° C. in two different beakers A and B, respectively. Then 7.5 ml of 2% Alhydrogel [Al(OH)$_3$] and 2.25 ml of tranexamic acid (TEA) coupled to beads (which specifically removes plasmin and/or plasminogen from the FDC preparation as generally disclosed in International Patent Application Publication No. WO 2013/001524) were added to each beaker with continuous stirring. 30 ml of pooled human plasma (cryo-poor plasma) were added to the mixture in beaker B.

FDC was prepared as follows: 80 g of frozen FDC were mechanically ground into small pieces (<1 cm) by using a blender at 2 cycles of 20 sec. each with a break of 20 sec. between the cycles. 30 g of ground FDC were added to each beaker (A and B) with continuous stirring at a temperature of 30-32° C. The ratio of FDC to plasma in sample B was 1:1 (w/v). After 10 min., the pH of the mixtures was adjusted to 7.2-7.3 using 0.1M NaOH and the mixture was left to solubilize with stirring for 90 minutes. Once the FDC was solubilized in both beakers, the non-resuspended/nonsolubilized particles were precipitated by centrifugation 17,000 g/25 minutes. The supernatants were clarified by filtration through a 1.2 µm filter. The clarified supernatants were supplemented to have final concentrations of 1 mM CaCl$_2$ and 120 mM Glycine, and the samples A and B (supernatants) were stored at ≤−30° C. until assayed for stability (Example 2) and for anti-B19 antibodies content (Example 4). The fibrinogen concentration in samples A and B was in the range 15-40 mg/ml.

Example 2: Stability of a Plasma-Supplemented Concentrated Fibrinogen Preparation Obtained from FDC The unsupplemented (A) and plasma-supplemented (B) fibrinogen samples of Example 1, above, were tested for fibrinogen stability as follows:

The samples were kept at room temperature 20-25° C. for up to 5 days. The stability of the fibrinogen was assessed using the Clauss method (as described supra). The results are summarized in Table 1.

TABLE 1

Stability of plasma-supplemented and non-supplemented fibrinogen.

| | Fibrinogen by Clauss (mg/ml) for the stability period | | | |
|---|---|---|---|---|
| | Day 0 | Day 1 | Day 4 | Day 5 |
| Sample A (without plasma) | 17 | 14 | 14 | 6 |
| Sample B (with plasma) | 22 | 26 | 24 | 24 |

Table 1 shows that the plasma-supplemented sample (Sample B) remained stable for the 5 days of the study while the parallel un-supplemented sample (Sample A) showed poor stability.

The results were confirmed in several experiments using different batches of FDC and different batches of plasma.

Example 3: Stability of a Plasma-Supplemented Concentrated Fibrinogen Obtained from Cryoprecipitate Plasma was added to a concentrated fibrinogen preparation obtained from cryoprecipitate to assess the effect of plasma on protein stability (e.g. reduction of proteolysis). The cryoprecipitate-derived concentrated fibrinogen preparation was prepared by dissolving the cryoprecipitate, adding aluminum hydroxide, subjecting to S/D treatment, and removing S/D material by oil extraction and reversed phase column (as generally described in WO 93/05822 and WO 94/22503). In this example, the concentrated fibrinogen preparations were neither subjected to TEA for removing plasmin/plasminogen nor to protease inhibitors. Samples from two batches of concentrated fibrinogen preparations (about 30 mg/ml) were collected and incubated with or without added plasma at 37° C. (or kept frozen) and tested for protein integrity using SDS-PAGE. The plasma used was a plasma unit collected by plasmapheresis from a donor. The composition of the Dilution Buffer was 120 mM NaCl; 10 mM Sodium Citrate; 120 mM Glycine; 95 mM Arginine hydrochloride; 1 mM Calcium Chloride.

The concentrated fibrinogen preparations and plasma were thawed and the following aliquots (4×200 µl) were prepared for each of the following four groups:

I. 37° C. storage—100 µl fibrinogen preparation+100 µl Plasma.

II. 37° C. storage—100 µl fibrinogen preparation+100 µl Dilution Buffer.

III. −80° C. storage—100 µl fibrinogen preparation+100 µl Plasma.

IV. −80° C. storage—100 µl fibrinogen preparation+100 µl Dilution Buffer.

The samples were stored at −80° C. or at 37° C. according to the above scheme for 5 days. After 5 days incubation, the samples from the four groups were analyzed by SDS-PAGE.

The SDS-PAGE procedure was carried out as follows:

One liter running buffer was prepared by diluting 950 ml DDW with 50 ml MOPS running buffer ×20 (Life Technologies, NP0001). The composition of the sample loading mix is shown in Table 2.

TABLE 2

Sample composition for SDS-PAGE analysis.

| Composition of the sample loading mix | microL (uL) |
|---|---|
| DDW | 6 |
| Sample Buffer[1] | 2.5 |
| Reducing agent[2] | 1 |
| Sample | 0.5 |
| Total | 10 |

[1]Nupage Sample buffer × 4 (Invitrogen NP0007).
[2]Nupage reducing agent × 10 (Invitrogen NP0009).

All the samples were heated at 95° C. for 5 min and centrifuged. The gel (NuPAGE 12% Bis-Tris Gel, Life Technologies NP0314BOX) was loaded with 10 µl diluted sample per lane. The gel ran for 40 min at 200V. The gel was washed thrice with DDW and stained with Instant Imperial Protein Stain (Thermo, 26145) for at least 1 hour. Distaining was carried out with DDW washes and the gel was dried overnight. Results of SDS-PAGE are shown in FIG. 1.

FIG. 1 shows a comparison between concentrated fibrinogen samples which were un-supplemented (lanes 2 and 4) or plasma-supplemented (lanes 1 and 3) and kept for 5 days at 37° C. (lanes 1 and 2) or at −80° C. (lanes 3 and 4), as assayed by SDS-PAGE.

Surprisingly, the results show that addition of plasma led to a marked reduction in the appearance of the low molecular weight bands and to an increase in the intact fibrinogen bands (see FIG. 1, lane 1 vs. lane 2).

Example 4: Quantification of Anti-B19 Antibodies in Plasma-Supplemented Fibrinogen Disclosed in Example 1

The quantification of B19 specific antibodies was carried out using the parvovirus B19-IgG ELISA Kit (BIOTRIN), a sandwich ELISA for the detection of IgG class parvovirus B19 antibodies in human serum plasma. The assay was carried out according to the manufacturer's instructions. The results obtained for samples A and B are summarized in Table 3.

TABLE 3

B19 Abs in tested samples.

| Tested sample | anti-B19 Abs (IU/ml) |
|---|---|
| Fibrinogen without plasma supplementation (sample A) | 2.0 |
| Fibrinogen with plasma supplementation (sample B) | 4.8 |

Table 3 shows that both samples have anti-B19 Abs present but the amount of anti-B19 Abs in the fibrinogen sample supplemented with plasma (sample B) is significantly higher than in the un supplemented sample (sample A) (4.8 IU/ml vs. 2.0 IU/ml).

Example 5: Processing of Plasma-Supplemented Fibrinogen

The plasma-supplemented fibrinogen of Example 1 was processed (essentially as in International Patent Application Publication No. WO 2013/001524) to include two orthogonal viral inactivation steps, removal of plasmin and plasminogen, concentration, formulation and sterile filtration. The final formulation contained a fibrinogen concentration in the range of 50-90 mg/ml.

Example 6: In-Vivo Assessment of Plasma-Supplemented Fibrinogen Formulation as a Component of Fibrin Sealant The rat kidney hemostasis model is a common model to test hemostasis (Raccuia J S et al., Comparative efficacy of topical hemostatic agents in a rat kidney model. Am J Surg. 1992. 163(2):234-8). Briefly, the kidney was dissected out of the side of the peritoneum and pads were placed around it to soak up blood. A clamp was placed on the blood vessels supplying the kidney and a traverse cut was made through the kidney. A sealant formulation comprising a plasma-supplemented fibrinogen component (prepared as in Example 5) and a thrombin component (as the thrombin component in EVICEL fibrin sealant) were used in a 1:1 ratio. The sealant was applied and the clamp removed. Bleeding was assessed over a one hour period, after which the total amount of bleeding was weighed. Subsequently, the sealant was scraped off and the bleeding allowed to resume and quantified as low, medium, or high (to assess whether there was still a bleeding potential). All rats were infused with 300 IU heparin/kg animal weight to prevent spontaneous hemostasis.

The results showed that fibrin sealant comprising a plasma supplemented fibrinogen component achieved effective hemostasis.

Although various embodiments have been described herein, many modifications and variations to those embodiments may be implemented. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Citation or identification of any reference in this application shall not be construed as an admission that such reference is available as prior art to the invention.

Section headings are used herein to ease understanding of the specification and should not be construed as necessarily limiting.

The invention claimed is:

1. A method of preparing a stable liquid fibrinogen formulation, comprising mixing a concentrated fibrinogen preparation and a pooled plasma source, wherein: a) the concentrated fibrinogen preparation is depleted of plasmin and/or plasminogen, and is selected from the group consisting of a plasma cryoprecipitate, plasma acid-precipitate, plasma chill-precipitate, plasma aluminum hydroxide precipitate, plasma glycine precipitate, plasma ethanol precipitate, plasma heparin precipitate, and combinations thereof; b) the pooled plasma source comprises at least one protease selected from plasmin and plasminogen and is selected from the group consisting of thrombin depleted plasma, factor depleted plasma, and a combination thereof; c) the concentrated fibrinogen preparation and the plasma source are mixed in a ratio of about 3:1 to about 1:3, about 2:1 to about 1:2, or about 1:1, respectively, thereby obtaining a mixture thereof; d) the mixture is kept stored for 1-5 days; and wherein: (e) said plasma is not platelet rich plasma.

2. The method of claim 1, wherein the fibrinogen concentration in the concentrated fibrinogen preparation is in the range of about 10 mg/ml to 200 mg/ml.

3. The method of claim 1, wherein the fibrinogen concentration in the concentrated fibrinogen preparation is in the range of about 10 mg/ml to 150 mg/ml.

4. The method of claim 1, wherein the cryoprecipitate is a Factor VIII-depleted cryoprecipitate.

5. The method of claim 1, wherein the concentrated fibrinogen preparation and the plasma are mixed in a ratio of about 1:1.

* * * * *